United States Patent [19]

Kostlan et al.

[11] Patent Number: 5,101,030

[45] Date of Patent: Mar. 31, 1992

[54] 9-DEAZAGUANINES

[75] Inventors: Catherine R. Kostlan; Jagadish C. Sircar, both of Ann Arbor, Mich.

[73] Assignee: Warner-Lambert Company, Morris Plains, N.J.

[21] Appl. No.: 606,214

[22] Filed: Oct. 31, 1990

Related U.S. Application Data

[60] Division of Ser. No. 478,610, Feb. 12, 1990, Pat. No. 4,988,702, which is a division of Ser. No. 336,585, Apr. 10, 1989, Pat. No. 4,923,872, which is a continuation of Ser. No. 117,352, Nov. 12, 1987, abandoned, which is a continuation-in-part of Ser. No. 59,419, Jun. 18, 1987, abandoned, which is a continuation-in-part of Ser. No. 900,486, Aug. 26, 1986, abandoned.

[51] Int. Cl.$^5$ .................. C07D 239/36; C07D 239/47; C07D 487/04

[52] U.S. Cl. .................. 544/319; 544/320; 544/321; 544/280

[58] Field of Search ............... 544/319, 320, 321, 280

[56] References Cited

PUBLICATIONS

Modern Synthetic Reactions, 2nd Ed. (1972), pp. 4,8 and 9, Benjamin/Cummings Publ. Co., Menlo Park, Calif.

Primary Examiner—John M. Ford
Attorney, Agent, or Firm—Joan Thierstein

[57] ABSTRACT

The present invention is novel derivatives of pyrrolo [3,2-d]pyrimidines and pharmaceutical compositions and methods of use therefor. The derivatives are inhibitors of purine nucleoside phosphorylase selectively cytotoxic to T-cells but not to B-cells in the presence of 2'-deoxyguanosine and, therefore, are for use in the treatment of autoimmune diseases, gout, psoriasis or rejection of transplantation.

4 Claims, No Drawings

9-DEAZAGUANINES

This is a divisional of U.S. application Ser. No. 07/478,610, filed Feb. 12, 1990, now U.S. Pat. No. 4,988,702 which is a divisional of U.S. application Ser. No. 07/336,585, filed Apr. 10, 1989, now U.S. Pat. No. 4,923,872, which is a continuation of U.S. application No. 07/117,352, filed Nov. 12, 1987, now abandoned, which is a continuation-in-part of U.S. application Ser. No. 07/059,419, filed June 18, 1987, now abandoned which is a continuation-in-part of U.S. application Ser. No. 06/900,486, filed Aug. 26, 1986, now abandoned.

BACKGROUND OF THE INVENTION

Various purine derivatives are known including guanine derivatives having activity as inhibitors of purine nucleoside phosphoxylase (PNP-4) 767,202 filed Aug. 22, 1985, which is a continuation of U.S. Ser. No. 660,152 filed Oct. 12, 1984, now abandoned. Selected guanine derivatives previously known are also disclosed in the application. Therefore, U.S. Ser. No. 767,202 is incorporated herein by reference.

More specifically the following pyrrolo[3,2-d]-pyrimidin-4-ones having the Formula

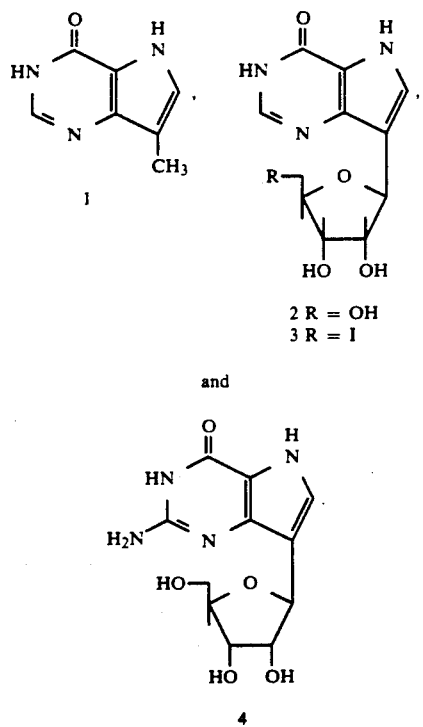

are known. The compound of Formula 1 is disclosed in *J. Org. Chem.*, 1979, 44:3826 and the compounds of Formula 2, 3, and 4 are disclosed by J. D. Stoeckler, et al., *Cancer Res.*, 1986, 46:1774). Further, Stoeckler, et al disclose PNP activity for compounds of the Formula 2, 3, and 4. These compounds differ from the present invention by an aryl or heteroaryl substituent compared to the methyl in the compound of Formulae 1 and the sugar moiety in the compounds of Formula 2, 3, and 4. Thus, the present invention are compounds which are not obvious variants thereof.

SUMMARY OF THE INVENTION

The present invention relates to a compound of the Formula (I)

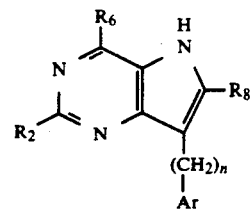

Wherein $R_6$ is OH or SH; $R_2$ is hydrogen or $NH_2$, $R_8$ is hydrogen or $NH_2$, n is an integer of zero through four, preferably one, and Ar is (i) phenyl unsubstituted or substituted by halogen, alkyl of from one to four carbon atoms, hydroxy, alkoxy of one to four carbon atoms, or trifluoromethyl; (ii) 2- or 3-thienyl; or (iii) 2- or 3-furanyl; or a pharmaceutically acceptable acid or base addition salt thereof.

The present invention also includes methods of manufacturing and a pharmaceutical composition for treating autoimmune diseases; such as arthritis, systemic lupus erythematosus, inflammatory bowel diseases, juvenile diabetes, myasthenia gravis, multiple sclerosis, gout and gouty arthritis, as well as psoriasis, viral infections, and cancer, or rejection of transplantation, comprising an immunomodulator or antirejection effective amount; such as a cytotoxic to T-cell amount, of a compound of the Formula I with a pharmaceutically acceptable carrier. Thus, the invention is also a method of treating an autoimmune disease, psoriasis, or rejection of transplantation as listed above comprising administering to a host, such as a mammal including a human suffering from an autoimmune disease or psoriasis or transplantation rejection advantageously affected by T-cell toxicity of the compounds of the present invention comprising administering an effective amount of a compound of the Formula I in unit dosage form. It is understood, an ordinarily skilled physician would begin treatment with a nontoxic and less than effective amount and increase the dose until the desired effect is obtained exercising care to administer an amount less than the amount toxic to the host of the disease.

The present invention also includes novel intermediates as follows:

(1) A compound of the Formula (II)

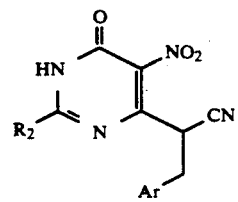

Wherein $R_2$ and Ar is as defined above; and (2) A compound of the Formula (III)

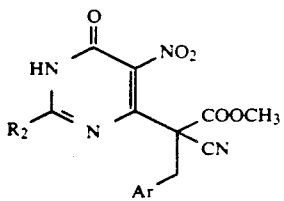

Wherein $R_2$ and Ar is as defined above.

The novel processes of the present invention is as follows:

(A) A process for the preparation of a compound of the Formula I comprising the treatment of a compound of the Formula II as defined above with $Na_2S_2O_4$ and then a basic solution such as 1N NaOH in the presence of heat to obtain the compound of Formula I wherein $R_8$ is amino. Alternatively the nitro compound II as defined above can be reduced catalytically to give I and overreduction of II in the presence of a catalyst and hydrogen to obtain a compound of the Formula I wherein $R_8$ is hydrogen, and, if desired, where $R_6$ is O or OH, converting said compound to a compound where $R_6$ is S or SH by methods analogous to those known in the art. Such conversion may be performed on the compound of either Formula I wherein $R_8$ is $NH_2$ or Formula I wherein $R_8$ is H. Finally, the compound of Formula I may be used to prepare a pharmaceutically acceptable acid addition or base salt thereof.

(B) A process for the preparation of a compound of the Formula II as defined above comprising the treatment of a compound of the Formula III as defined above with (1) a base, such as a 1N NaOH solution at about room temperature and then (2) an acid, such as hydrochloric acid to obtain the compound of Formula II.

(C) A process for the preparation of a compound of the formula III as defined above which comprises contacting a compound of the Formula III as defined above which comprises contacting a compound of the Formula (IV)

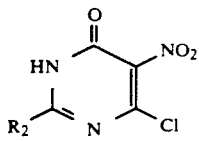

Wherein $R_2$ is as defined above; with a compound of the formula (V)

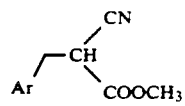

where in Ar is as defined above; in the presence of sodium hydride in dimethylformamide or potassium t-butoxide in DMSO or similar conditions.

Under certain circumstances it may be necessary to protect either the N or O of intermediates in the above noted process with suitable protecting groups which are known. Introduction and removal of such suitable oxygen and nitrogen protecting groups are well known in the art of organic chemistry; see for example, (1) "Protective Groups in Organic Chemistry," J. F. W. McO-mie, ed., (New York, 1973), pp 43ff, 95ff; (2) J. F. W. McOmie, *Advances in Organic Chemistry*, Vol. 3, 191-281 (1963); (3) R. A. Borssonas, *Advances in Organic Chemistry*, Vol. 3, 159-190 (1963); and (4) J. F. W. McOmie, Chem. & Ind., 603 (1979).

Examples of suitable oxygen protecting groups are benzyl, t-butyldimethylsilyl, methyl, isopropyl, ethyl, tertiary butyl, ethoxyethyl, and the like. Protection of an N-H containing moiety is necessary for some of the processes described herein for the preparation of compounds of this invention. Suitable nitrogen protecting groups are benzyl, triphenylmethyl, trialkylsilyl, trichloroethylcarbamate, trichloroethyoxycarbonyl, vinyloxycarbamate, and the like.

Under certain circumstances it is necessary to protect two different oxygens with dissimilar protecting groups such that one can be selectively removed while leaving the other in place. The benzyl and t-butyldimethylsilyl groups are used in this way; either is removable in the presence of the other, benzyl being removed by catalytic hydrogenolysis, and t-butyldimethylsilyl being removed by reaction with, for example, tetra-n-butylammonium fluoride.

In the process described herein for the preparation of compounds of this invention the requirements for protective groups are generally well recognized by one skilled in the art of organic chemistry, and accordingly the use of appropriate protecting groups is necessarily implied by the processes of the charts herein, although not expressly illustrated.

The products of the reactions described herein are isolated by conventional means such as extraction, distillation, chromatography, and the like.

The salts of compounds of Formula I described above are prepared by reacting the appropriate base with a stoichiometric equivalent of the acid compounds of Formula I to obtain pharmacologically acceptable salts thereof.

The compounds of this invention may also exist in hydrated or solvated forms.

The novel processes in steps beginning with (C) and continuing through (B) and (A) above may be conducted in a one part process. However, it is preferred to separate the product of Formula III and the product of Formula II before proceeding to the next process step.

DETAILED DESCRIPTION

The compounds of Formula I and intermediates of Formula II and III of the present invention exist in tautomeric forms as purines or guanines as illustrated below. Both forms are included as part of the invention and are indiscriminately described in the specification.

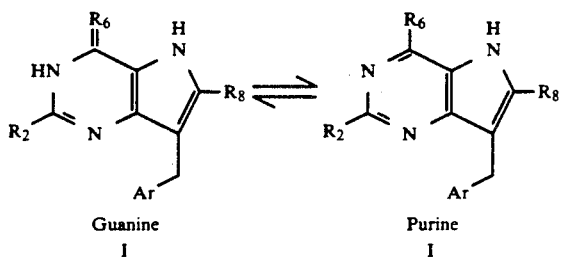

Guanine I    Purine I wherein $R_6$ is OH or SH

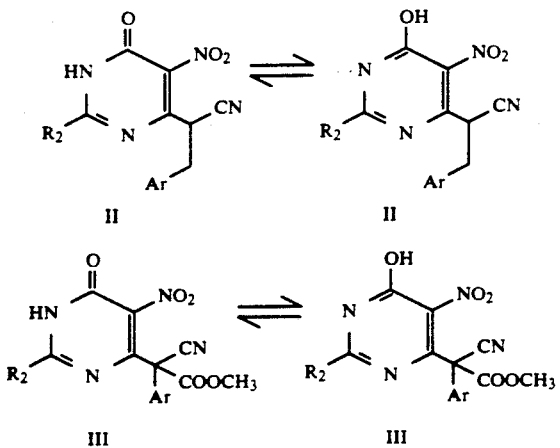

The term "alkyl of one to four carbon atoms" means a straight or branched hydrocarbon chain up to four carbon atoms such as, for example, methyl, ethyl, propyl, isopropyl butyl, isobutyl, secondary butyl or tertiary butyl. "Alkoxy of one to four carbon atoms includes methoxy, ethoxy, propoxy, butoxy and isomers thereof. Halogen is fluorine, chlorine, bromine, or iodine.

The compounds of Formula I are useful both in the free base form, in the form of base salts where possible, and in the form of acid addition salts. The three forms are within the scope of the invention. In practice, use of the salt form amounts to use of the base form. Appropriate pharmaceutically acceptable salts within the scope of the invention are those derived from mineral acids such as hydrochloric acid and sulfuric acid, and organic acids such as methanesulfonic acid, benzenesulfonic acid, p-toluenesulfonic acid, isothienic acid, and the like, giving the hydrochloride, sulfate, methanesulfonate, benzenesulfonate, p-toluenesulfonate, and the like, respectively or those derived from bases such as suitable organic and inorganic bases. Examples of suitable inorganic bases for the formation of salts of compounds of this invention include the hydroxides, of ammonia, sodium, lithium, potassium, calcium, magnesium, aluminum, zinc, and the like.

Salts may also be formed with suitable organic bases. Bases suitable for the formation of pharmaceutically acceptable base addition salts with compounds of the present invention include organic bases which are nontoxic and strong enough to form such salts. These organic bases form a class whose limits are readily understood by those skilled in the art. Merely for purposes of illustration, the class may be said to include mono-, di-, and trialkylamines, such as methylamine, dimethylamine, and triethylamine; mono-, di-, or trihydroxyalkylamines such as mono-, di-, and triethanolamine; amino acids such as arginine, and lysine; guanidine; N-methylglucamine; L-glutamine; N-methylpiperazine; morpholine; ethylenediamine; N-benzylphenethylamine; tris(-hydroxymethyl)aminomethane; and the like. (See for example, "Pharmaceutical Salts," *J. Pharm. Sci.*(1977) 66(1):1–19.)

The acid addition salts of said basic compounds are prepared either by dissolving the free base of compound I in aqueous or aqueous alcohol solution or other suitable solvents containing the appropriate acid or base and isolating the salt by evaporating the solution, or by reacting the free base of compound I with an acid as well as reacting compound I having an acid group thereon with a base such that the reactions are in an organic solvent, in which case the salt separates directly or can be obtained by concentration of the solution.

A preferred embodiment of the present invention is a compound of Formula I wherein $R_6$ is OH or SH; $R_2$ and $R_8$ are $NH_2$, n is one, and Ar is either phenyl or 2- or 3-thienyl. A more preferred embodiment is 2,6-diamino-3,5-dihydro-7-(phenylmethyl)-4H-pyrrolo[3,2-d]pyrimidin-4-one,2,6-diamino-3,5-dihydro-7-(2-thienylmethyl)-4H-pyrrolo[3,2-d]pyrimidin-4 -one or 2,6-diamino-3,5-dihydro-7-(3-thienylmethyl)-4H-pyrrolo[3,2-d]pyrimidin-4-one. Of these the most preferred is the latter of these three.

The compound of Formula I may generally be prepared according to the method shown in the following scheme.

SCHEME

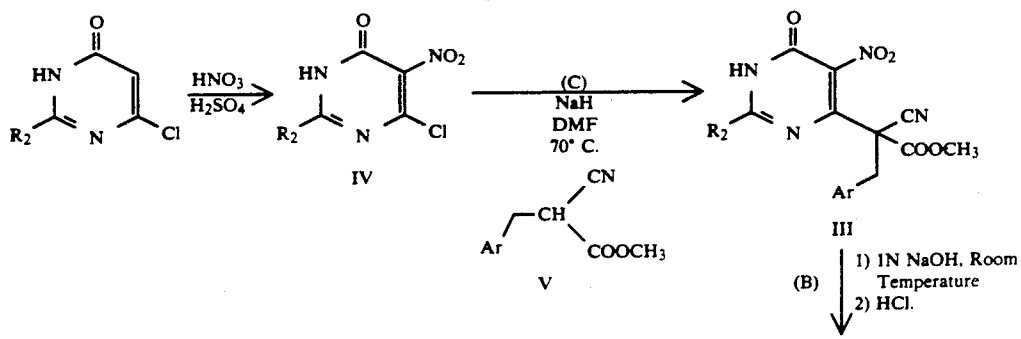

-continued
SCHEME

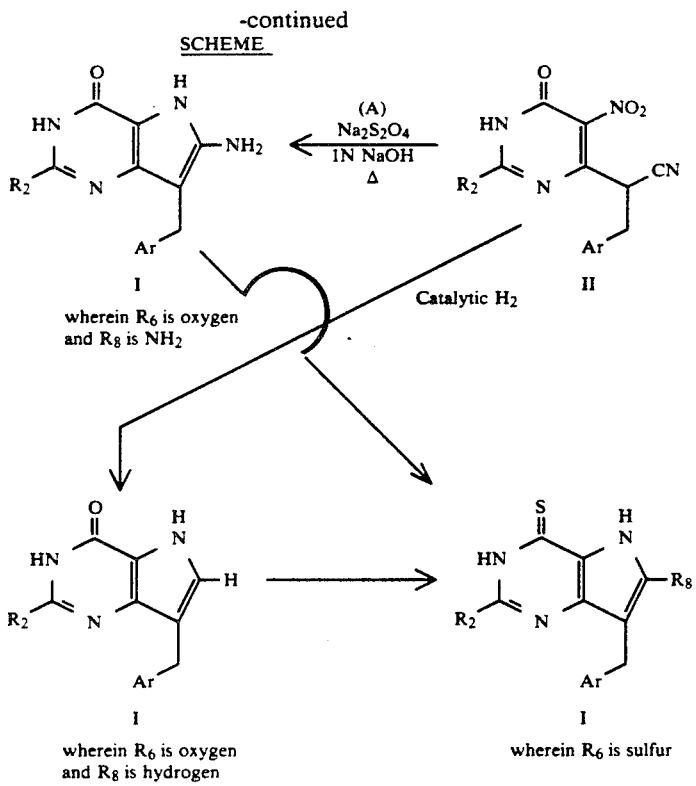

wherein $R_6$ is oxygen
and $R_8$ is hydrogen wherein $R_6$ is sulfur

Generally, the starting materials having the Formula IV and V are either commercially available or may be prepared by known methods. For example, the compounds of Formula IV may be prepared by a procedure described in *Synthetic Procedures in Nucleic Acid Chemistry* Vol. 1 (1973) page 94, and the compounds of Formula V may be prepared by procedures analogous to those described in U.S. Pat. No. 4,279,903 and references cited therein.

Further, the conditions for contacting the compounds V and IV of process (C) above include the dropwise addition of sodium hydride oil suspension to a solution of the compound V in a solvent such as dimethylformamide (DMF) followed by the further addition of a solution of the compound of formula IV also in a solvent such as DMF under a dry nitrogen atmosphere. The resulting reaction mixture is heated to from 60° to 90° C. for from 30 minutes to two hours and then acidified to about pH 3 or 4 with 1–6 N HCl. The condensation of process (c) may also be accomplished in a solvent, such as DMSO, and in the presence of t-butoxide.

The conditions of process (B) for treating the product of (C) having the Formula III as defined above are first treating a solution thereof with, for example, 1N NaOH at about room temperature followed by acidifiction with, for example 4N HCl to precipitate the product having the Formula II.

For process (A) a solution of the compound of Formula II in 1N NaOH is treated with sodium dithionite at from 70° to 95° C. and preferably 90° C. for from 10 to 60 minutes, preferably about 25 to 40 minutes and then again acidified to about pH 3 or 4 to provide crystals of the product of Formula I wherein $R_6$ is oxygen and $R_8$ is $NH_2$. Further catalytic reduction under conditions within those known to the artisan for similar reductions the Compound II wherein $R_6$ is oxygen and $R_6$ is amino or hydrogen is obtained.

The compounds having the Formula I of the present invention have been shown to exhibit significant enzyme inhibition activity and cytotoxic activity. In the purine nucleoside phosphorylase (PNP-4) enzyme assay, an $IC_{50}$ is achieved at a dose of about from 0.9 to 3.18 micromoles on selected compounds of the present invention. PNP-4 activity for the compounds of Formula I is measured radiochemically by measuring the formation of $[^{14}-C]$-hypoxanthine from $[^{14}-C]$inosine [Biomedicine, 33, 39 (1980)] using human erythrocyte as the enzyme source. An in vivo inhibition of purine nucleoside phophorylase (HPLC-1) enzyme assay is used essentially as disclosed in the Annals of New York Academy of Sciences, Volume 451, Page 313 (1985) to further show the activity of the compounds of Formula I of the present invention. The same compounds also were found by a standard test (HTBA-1) [Science, 214, 1137, (1981)] to be selectively cytotoxic for T-cells in the presence of 2'-deoxyguanosine at a similar concentration range and nontoxic to B-cell in the presence of the same amount of 2'-deoxyguanosine demonstrating utility for the compounds of Formula I as described herein. Since removal of T-cells or modulation of T-cells are beneficial in the treatment of autoimmune diseases, these compounds being selectively cytotoxic to T-cells will, therefore, be useful in their treatment. 8-aminoguanosine, a known PNP-inhibitor, has been shown to be efficacious for inhibiting rejection of skin graft in dogs [J. B. Benear, et al, Transplantation, 1986, 41:274]. Clinically it has been shown that modulation and/or removal of T-cells by throacic duct drainage, lymphapheresis or total lymphoid irradiation gave partial to complete relief from rheumatoid arthritis in patients who were totally refractory to other forms of therapy (A. Tanay, et al, *Arthritis and Rheumatism*, Vol. 30, No. 1, p 1 (1987). S. Strober, et al, *Annual of Internal Medicine*, V-102, No. 4, 441–449 (1985); H. G. Nusslein, et al, *Arthritis and Rheumatism*, V-28, No. 11, 1205–1210 (1985); E. Brahn, et al, ibid, V-27, No. 5, 481–487 (1984), and J. Karsh, et al, ibid, V-24, No. 7, 867–873 (1981)). Cyclosporin A, A T-cell modulator, showed beneficial effects in the treatment of juvenile diabetes. (A. Assan, et al, The Lancet, January 12, p 67, (1985). Additionally, cyclosporin A is presently the drug of choice for the prevention of transplant rejection, (R. M. Merion, et al, *New Eng. J. Med.*, (1984), 148). More recently, cyclosporin A is shown to be useful to treat psoriasis. Further, it is suggested the cyclosporin therapy is shown to markedly reduce activated T-cells in psoriatic lesions. Therefore, it is reasonable to believe the basis of the successful treatment of psoriasis is modulation of T-cell activity. (See C. N. Ellis, et al, JAMA. V-256, No. 22, Dec. 12, 1986, pp 3110–3116.) Finally, cyclosporin A is shown to be efficacious in rheumatoid arthritis. (M. E. Weinblatt, et al, *Arthritis and Rheumatism*, V-30, No. 1 pp 11–17 (January, 1987); O. Forre, et al, *Arthritis and Rheumatism*, V-30, No. 1, pp 88–92 (January, 1987); M. Dougados, et al, *Arthritis and Rheumatism*, Vol. 30, No. 1, pp 83–87 (January, 1987);

Representative examples from the present invention are shown in the following activity table to provide the activity discussed above.

ACTIVITY TABLE

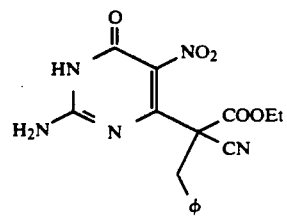

| Number | $R_8$ | Ar* | PNP-4 $IC_{50}(\mu M)$ | HTBA-1 T-Cell + 10 $\mu M$ 2'-d Gua; $IC_{50}$ $\mu M$ | HPLC-1 (mg/kg; PO) Inosine ($\mu M$) | Guanosine |
|---|---|---|---|---|---|---|
| 3 | $NH_2$ | $C_6H_5$ | 1.6 | 1.7 | 2.93 | 0.54(100) |
| 6 | $NH_2$ | 2-Th | 1.0 | 1.9 | 2.64 | 0.36(100) |
| 9 | $NH_2$ | 3-Th | 0.9 | 2.3 | 2.62 | 0.26(150) |
| 13 | $NH_2$ | 2-methoxyphenyl | 3.18 or 3.09 | | | |

Th = Thiophene

In vivo studies based on the above noted disclosures maybe used to determine activity in the particular disease states noted.

Since T-cells play a central role in immune response, use of the compounds of the invention is contemplated for the immunoregulation to prevent rejection in transplantation or in the treatment of psoriasis and in the treatment of autoimmune disease such as rheumatoid arthritis, systemic lupus erythrematosus, inflammatory bowel disease, multiple sclerosis, myasthemia gravis, gout or gouty arthritis juvenile diabetes, cancer, and viral diseases. The present invention thus includes compositions containing a compound of Formula I in treating rejection of transplantation or disease such as psoriasis in humans or autoimmune disease characterized by abnormal immune response in primates or humans. According to this aspect of the invention, the properties of the compounds of the invention are utilized by administering to a warmblooded animal an effective amount of a pharmaceutical composition containing as the active ingredient at least about 0.1 percent by weight, based on the total weight of the composition of at least one such compound of the invention.

Pharmaceutical compositions of the invention can be formulated in any suitable way, preferably with an inert carrier for administration orally, parenterally, ophthalmically, topically, or by suppository.

For example, the compounds of the present invention are formulated into dosage forms such as tablets or syrups by blending with an inert pharmaceutical carrier such as lactose or simple syrup by methods well known in the art. For injectable dosage forms, they are formulated with vehicles such as water, propylene glycol, peanut oil, sesame oil, and the like. In these dosage forms, the active ingredient is from about 0.05 grams to 0.5 grams per dosage unit.

The present invention is further illustrated by way of the following examples.

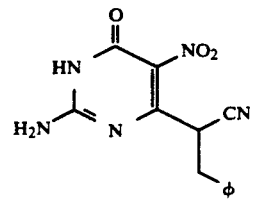

EXAMPLE 1

2-Amino-α-cyano-1,6-dihydro-5-nitro-α-(phenylmethyl)-6-oxo-4-pyrimidineacetic acid, ethyl ester A solution of ethyl 2-cyano-3-phenyl-propionate (JCS, 1944, 13) (6.0 g) in DMF (25 mL) is added dropwise to a suspension of sodium hydride (1.2 g, 60% suspension in oil, washed with hexane) in DMF (25 mL) under an atomosphere of dry $N_2$. The reaction mixture is stirred for 15 min at room temperature and then a solution of 2-amino-6-chloro-5-nitro-4(3H)-pyrimidinone (Synthetic Procedures in Nucleic Acid, V-1, 1973, p. 94) (1.9 g, freshly crystallized from methanol) in DMF (50 mL) is added to the anion. The reaction mixture is heated at 65° C. for 24 h and then acidified to pH 3 with 1N HCl.

Most of the DMF is removed by evaporation on a rotary evaporator under high vacuum. The residual oil is partitioned between ethyl acetate (500 mL) and water. The organic layer is dried ($Na_2SO_4$) evaporated to a gummy solid. The residue is triturated with ether and collected by filtration. It is dried under vacuum to give 2-Amino-α-cyano-1,6-dihydro-5-nitro-α-(phenylmethyl)-6-oxo-4-pyrimidineacetic acid, ethyl ester as a partial hydrate (2.25 g, 62%).

EXAMPLE 2

2-Amino-1,6-dihydro-5-nitro-6-oxo-α-(phenylmethyl)-4-pyrimidineacetonitrile

A solution of 2-Amino-α-cyano-1,6-dihydro-5-nitro-α-(phenylmethyl)-6-oxo-4-pyrimidine-acetic acid, ethyl ester as prepared above (2.0 g) in 1N NaOH (100 mL) is stirred at room temperature for 1 h and is acidified with 4N HCl (30 mL). The precipitate is collected by filtration and dried under vacuum to give 2-Amino-1,6-dihydro-5-nitro-6-oxo-α-(phenylmethyl)-4-pyrimidineacetonitrile (600 mg, 36%).

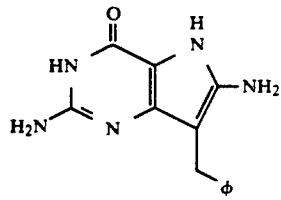

EXAMPLE 3

2,6-Diamino-3,5-dihydro-7-(phenylmethyl)-4H-pyrrolo[3,2-d]pyrimidin-4-one.

To a solution of 2-Amino-1,6-dihydro-5-nitro-6-oxo-o-(phenylmethyl)-4-pyrimidine acetonitrile as prepared above (10.0 g) in 1N NaOH (600 mL) is added sodium dithionite (35 g). The reaction mixture is heated at 90° C. for 35 min and is acidified to pH 4 with 4N HCl while still hot. The reaction mixture is cooled in an ice bath and the precipitate is collected by filtration. It is dried over P₂O₅ under vacuum (4.0 g). The crude (undecarboxy-ated) product is dissolved in 300 mL conc HCl and quickly filtered through a glass frit before it crystallized out. The resulting suspension is boiled for five minutes and cooled. The product 2,6-Diamino-3, 5-dihydro-7-(phenylmethyl)-4H-pyrrolo[3, 2-d]pyrimidin-4-one is collected by filtration (1.98 g, 23%) mp>250° C. (dec).

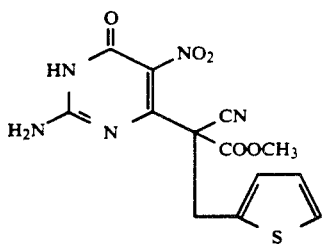

EXAMPLE 4

2-Amino-α-cyano-1,6-dihydro-5-nitro-6-oxo-α-(2-thienylmethyl)-4- pyrimidineacetic acid, methyl ester.

Sodium hydride (4.5 g, 60% suspension in oil washed with hexane) is suspended in dry DMF (50 mL) under an atmosphere of dry N₂ and a solution of methyl 2-cyano-3-(2-thienyl) propionate (U.S. Pat. No. 4,279,903) (22.0 g) in dry DMF (50 mL) is added dropwise when a dark blue solution is formed. A solution of freshly recrystallized 2-amino-6-chloro-5-nitro-4(3H)-pyrimidinone (8.57 g) in DMF (75 mL) is added in one portion. The reaction mixture is heated at 60° C. over-night and cooled and then is acidified to pH 5 with 1N HCl. It is poured into 1000 mL ethyl acetate and is extracted with water (4×300 mL). The organic layer is evaporated to near dryness and the residue is suspended in ether and collected by filtration. The crude product green. The solid is dried under vacuum to give 2-Amino-α-cyano-1,6-dihydro-5-nitro-6-oxo-α-(2-thienylmethyl)-4-pyrimidine-acetic acid, methyl ester.

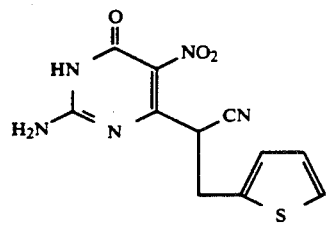

EXAMPLE 5

2-Amino-1,6-dihydro-5-nitro-6-oxo-α-(2-thienylmethyl)-4-pyrimidineacetonitrile.

A solution of 2-Amino-α-cyano-1,6-dihydro-5-nitro-6-oxo-α-(2-thienylmethyl)-4-pyrimidineacetic acid, ethyl ester as prepared above (5.0 g) in 1N NaOH (200 mL) is stirred at room temperature for 90 min. The reaction mixture is acidified to pH 1 with 4N HCl and stirred for 5 min. The reaction mixture is neutralized (pH 7) with 1N NaOH and the product 2-Amino-1,6-dihydro-5-nitro-6-oxo-α-(2-thienylmethyl)-4-pyrimidineacetonitrile (4.1 g, 98%) is collected by filtration.

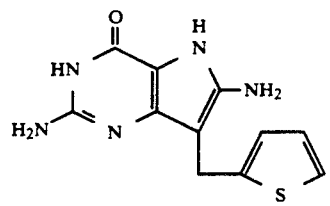

EXAMPLE 6

2,6-Diamino-3,5-dihydro-7-(2-thienylmethyl)-4H-pyrrolo[3,2-d]pyrimidin-4-one

To a solution of 2-Amino-1,6-dihydro-5-nitro-6-oxo-α-(2-thienylmethyl)-4-pyrimidine-acetonitrile as prepared above (4.0 g) in 1N NaOH (250 mL) is added sodium dithionite (17 g) and the reaction mixture is heated at 90° C. for 20 min. The reaction mixture is acidified to pH 2 with 4N HCl while still hot and filtered and then is cooled and neutralized with 1N NaOH. The resulting precipitate is collected by filtration and dried. The crude product is added to a stirred solution of conc HCl (150 mL) and the hydro-chloride salt is collected by filtration. The salt is dissolved in aq NaOH and reprecipitated with 1N HCl. Recrystallization from 2N HCl gave the analytical hydrochloride salt the monohydrate, of 2,6-Diamino-3, 5-dihydro-7-(2-thienylmethyl) -4H-pyrrolo[3,2-d]-pyrimidin-4-one (0.82, 19%), mp 220°-225° C. (dec).

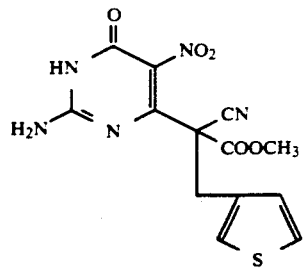

EXAMPLE 7

2-Amino-α-cyano-1,6-dihydro-5-nitro-6-oxo-α-(3-thienylmethyl)-4-pyrimidineacetic acid, ethyl ester Sodium hydride (5.7 g; 60% suspension in oil is washed with hexane) is suspended in dry DMF (50 mL) under an atmosphere of dry $N_2$ and a solution of methyl 2-cyano-3-(3-thienyl) propionate (U.S. Pat. No. 4,279,903) (28.0 g) in DMF (50 mL) is added dropwise. 2-Amino-6-chloro-5-nitro-4 (3H)-pyrimidinone (9.1 g, freshly recrystallized) in DMF (50 mL) is added. The reaction mixture is heated at 70° C. overnight, cooled, and then acidified to pH 4 with 1N HCl with ice bath cooling. The reaction mixture is diluted to 1000 mL with cold water and the resulting precipitate is collected by filtration. It is rinsed with hexane/ethylacetate and dried to give 2-Amino-α-cyano-1,6-dihydro-5-nitro-6-oxo-α-(3-thienylmethyl)-4-pyrimidine-acetic acid, ethyl ester (Ar=3-Th) (8.8 g, 52%).

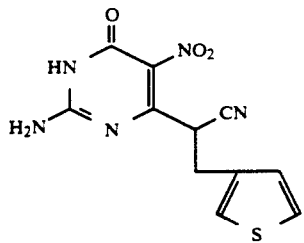

EXAMPLE 8

2-Amino-1,6-dihydro-5-nitro-6-oxo-α-(3-thienylmethyl)-4-pyrimidineacetonitrile

A solution of 2-Amino-α-cyano-1,6-dihydro-5-nitro-6-oxo-α-(3-thienyl-methyl)-4-pyrimidineacetic acid, ethyl ester in 1N NaOH (200 mL) is stirred for 2 h at room temperature and then acidified to pH 1 by the dropwise addition of conc HCl. The resulting suspension is warmed (45° C.) for 2 min and then cooled. The pH is adjusted to pH=3 with NH4OH. The solid is collected by filtration, washed with water, and dried under vacuum to give 2-Amino-1,6-dihydro-5-nitro-6-oxo-α-(3-thienylmethyl) -4-pyrimidineacetonitrile (3.03 g).

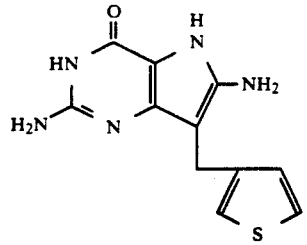

EXAMPLE 9

2,6-Diamino-3,5-dihydro-7-(3-thienylmethyl)-4H-pyrrolo-[3,2-d]pyrimidin-4-one

To a solution of 2-Amino-1,6-dihydro-5-nitro-6-oxo-α-(3-thienylmethyl)-4-pyrimidineacetonitrile prepared above (5.0 g) in 1N NaOH (300 mL) is added sodium dithionite (20 g). The reaction mixture is heated for 30 min at 90° C. and then is acidified (pH 1) with mono HCl while still hot. The reaction mixture is cooled and neutralized with ammonium hydroxide. The resulting precipitate is collected by filtration, washed with cold water and dried under vacuum. The crude product is added to 100 mL conc HCl in small portions with stirring and the hydrochloride salt is collected by filtration. The product is recrystallized from 1N HCl to give 2,6-Diamino-3,5-dihydro-7-(3-thienylmethyl)-4H-pyrrolo [3,2-d]pyrimidine-4-one as the monohydro-chloride salt (2.35 g), mp>85° C. (dec).

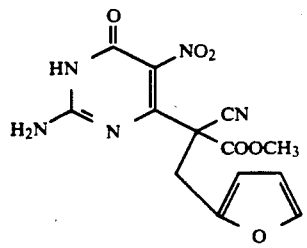

EXAMPLE 10

2-Amino-α-cyano-α-(2-furanylmethyl)-1,6-dihydro-5-nitro-6-oxo-4-pyrimidineacetic acid, ethyl ester Sodium hydride (8.4 g, 60% suspension in oil, washed with hexane) is suspended in dry DMF (100 mL) under an atmosphere of dry $N_2$ and a solution of methyl 2-cyano-3-(2-furanyl)propionate (U.S. Pat. No. 4,279,903) (37.6 g) in DMF (100 mL) is added dropwise. When the addition is complete, a clear red solution is formed. 2-Amino-6-chloro-5-nitro-4(3H)-pyrimidinone (recrystallized from methanol) (13.34 g) is added as a solid. The reaction mixture is heated at 100° C. for 1 h and at 65° C. overnight. The reaction mixture is cooled in an ice bath, acidified with 10% aq HCl and diluted with enough water to precipitate out the product 2-Amino-α-cyano-α-(2-furanylmethyl)-1,6-dihydro-5-nitro-6-oxo-4-pyrimidineacetic acid, ethyl ester. The product is collected by filtration and rinsed with water and ether (18.5 g).

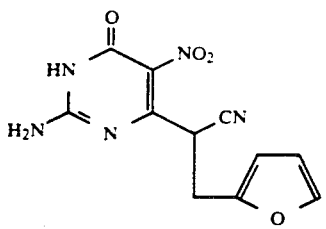

EXAMPLE 11

2-Amino-α-(2-Furanylmethyl)-1,6-dihydro-5-nitro-6-oxo-4-pyrimidineacetonitrile

A solution of 2-Amino-α-cyano-α-(2-furanylmethyl)-1,6-dihydro-5-nitro-6-oxo-4-pyrimidineacetic acid, ethyl ester (5.0 g) in 1N NaOH (200 mL) is stirred at room temperature for 2 h. The reaction mixture is acidified (pH 1) by the dropwise addition of conc HCl and is stirred at room temperature for 2 min. The precipitate is collected by filtration, washed with water, and dried to give 2-Amino-α-(2-Furanylmethyl)-1, 6-dihydro-5-nitro-6-oxo-4-pyrimidineacetonitrile (3.02 g 73%).

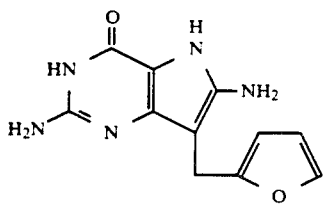

EXAMPLE 12

2,6-Diamino-3,5-dihydro-7-(2-furanylmethyl)-4H-pyrrolo [3,2-d]pyrimidin-4-one

To a solution of 2-Amino-α-(2-Furanylmethyl)-1,6-dihydro-5-nitro-6-oxo-4-pyrimidine-acetonitrile (4.0 g) in 1N NaOH (250 mL) is added sodium dithionite (16 g) and the reaction mixture is heated at 90° C. for 30 min. The reaction mixture is cooled in an ice bath and neutralized with 4N HCl. The resulting precipitate is collected by filtration and purified by a series of acid/base reprecipitations. First the product is reprecipitated from 1N NaOH by acidifying (pH 2) with a saturated solution of oxalic acid. This NaOH/oxalic acid reprecipitation is repeated. Then it is reprecipitated from 1N NaOH by adjusting pH to 11 with 4N HCl. The product 2,6-Diamino-3,5-dihydro-7-(2-furanylmethyl)-4H-pyrrolo[3,2-d ]pyrimidin-4-one is dried under vacuum.

EXAMPLE 13

The following compound is prepared according to the method of Example 3 above using appropriate corresponding starting materials: 2,6-diamino-3,5-dihydro-7-(2'-methoxyphenylmethyl)-4H-pyrrolo[3,2-d ]pyrimidin-4-one monohydrochloride with a third mole H$_2$O mp 215°-240° C. (dec).

We claim:

1. A compound of the Formula (II)

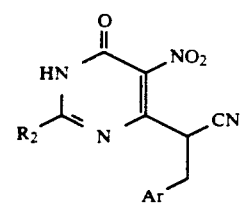

wherein R$_2$ is hydrogen or NH$_2$, and Ar is (i) phenyl unsubstituted or substituted by halogen, alkyl of from one to four carbons, hydroxy, alkoxy of one to four carbons, or trifluoromethyl, (ii) 2- or 3-thienyl, or (iii) 2- or 3-furanyl.

2. A compound of the Formula (III)

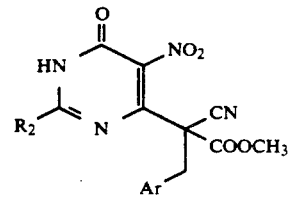

wherein R$_2$ is hydrogen or NH$_2$ and Ar is (i) phenyl unsubstituted or substituted by halogen, alkyl of from one to four carbons, hydroxy, alkoxy of from one to four carbon atoms, or trifluoromethyl, (ii) 2- or 3- thienyl, (iii) 2- or 3- furanyl.

3. A process of treating a compound of Formula (II)

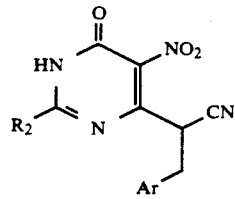

wherein R$_2$ is hydrogen or NH$_2$, and Ar is (i) phenyl unsubstituted or substituted by halogen, alkyl of from one to four carbon atoms, hydroxy, alkoxy of one to four carbon atoms, or trifluoromethyl, (ii) 2- or 3- thienyl, or (iii) 2- or 3- furanyl;
in a basic solution with sodium dithionite to obtain a compound of the formula (I)

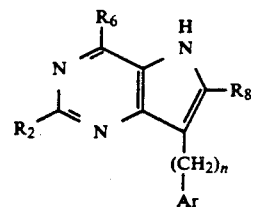

wherein R$_6$ is oxygen and R$_8$ is amino and R$_2$ and Ar are as defined as above; and alternatively further a) treating the compound of the formula II as defined above or b) treating the compound of the formula I wherein R$_6$ is oxygen and R$_8$ is amino; with hydrogen in the presence of a catalyst to obtain a compound of the formula I wherein R$_6$ is oxygen and R$_8$ is hydrogen.

4. A process of claim 3 wherein the basis solution is a 1N NaOH solution.

* * * * *